(12) United States Patent
Mayer et al.

(10) Patent No.: US 10,390,957 B2
(45) Date of Patent: Aug. 27, 2019

(54) DEVICE FOR REPAIRING A HUMAN OR ANIMAL JOINT

(71) Applicant: SpineWelding AG, Schlieren (CH)

(72) Inventors: Jörg Mayer, Niederlenz (CH); Marcel Aeschlimann, Ligerz (CH); Mario Lehmann, Les Pommerats (CH); Andreas Wenger, Muri b. Bern (CH); Stephanie Goebel-Mehl, Mettmenstetten (CH)

(73) Assignee: SPINEWELDING AG, Schlieren (CH)

( * ) Notice: Subject to any disclaimer, the term of this patent is extended or adjusted under 35 U.S.C. 154(b) by 108 days.

(21) Appl. No.: 15/415,033

(22) Filed: Jan. 25, 2017

(65) Prior Publication Data

US 2017/0128214 A1 May 11, 2017

Related U.S. Application Data

(62) Division of application No. 13/823,287, filed as application No. PCT/CH2011/000221 on Sep. 20, 2011, now Pat. No. 9,585,756.

(Continued)

(51) Int. Cl.
*A61F 2/44* (2006.01)
*A61F 2/30* (2006.01)
(Continued)

(52) U.S. Cl.
CPC ............... *A61F 2/30* (2013.01); *A61B 17/70* (2013.01); *A61F 2/30771* (2013.01);
(Continued)

(58) Field of Classification Search
CPC .......... A61F 2/44; A61F 2/4425; A61F 2/443; A61F 2/30; A61F 2002/30637;
(Continued)

(56) References Cited

U.S. PATENT DOCUMENTS 4,997,432 A * 3/1991 Keller .................. A61B 17/025
600/219
5,314,491 A 5/1994 Thongpreda
(Continued)

FOREIGN PATENT DOCUMENTS

JP 2007-519479 7/2007
JP 2008-541930 11/2008
(Continued)

*Primary Examiner* — Seema Mathew
(74) *Attorney, Agent, or Firm* — Rankin, Hill & Clark LLP

(57) ABSTRACT

A human or animal joint is treated by introduction of a device between the suitably prepared articulating surfaces of the joint, and the device is anchored in both these articular surfaces with a material having thermoplastic properties. For allowing at least limited articulation of the joint after implantation, the device includes two articulating portions, wherein one of the articulating portions is anchored in each articulating surfaces of the joint. On implantation a proximal face of the device is contacted with a vibrating tool and the vibration is transmitted through parts of the device to locations in which the material having thermoplastic properties is near the bone tissue of the articulating surfaces of the joint and in which liquefaction is desired. The liquefied material penetrates the bone tissue and, on re-solidification forms a positive fit connection between the device and the bone tissue.

8 Claims, 3 Drawing Sheets

Related U.S. Application Data

(60) Provisional application No. 61/384,922, filed on Sep. 21, 2010.

(51) Int. Cl.
 *A61B 17/70* (2006.01)
 *A61F 2/42* (2006.01)
 *A61F 2/46* (2006.01)
 *A61F 2/40* (2006.01)

(52) U.S. Cl.
 CPC ............ *A61F 2/442* (2013.01); *A61F 2/4405* (2013.01); *A61F 2/4425* (2013.01); *A61F 2/30988* (2013.01); *A61F 2/4225* (2013.01); *A61F 2/4241* (2013.01); *A61F 2/4611* (2013.01); *A61F 2002/307* (2013.01); *A61F 2002/30062* (2013.01); *A61F 2002/30065* (2013.01); *A61F 2002/30067* (2013.01); *A61F 2002/3082* (2013.01); *A61F 2002/30131* (2013.01); *A61F 2002/30367* (2013.01); *A61F 2002/30469* (2013.01); *A61F 2002/30472* (2013.01); *A61F 2002/30476* (2013.01); *A61F 2002/30563* (2013.01); *A61F 2002/30581* (2013.01); *A61F 2002/30584* (2013.01); *A61F 2002/30604* (2013.01); *A61F 2002/30607* (2013.01); *A61F 2002/30624* (2013.01); *A61F 2002/30934* (2013.01); *A61F 2002/30996* (2013.01); *A61F 2002/4092* (2013.01); *A61F 2002/4096* (2013.01); *A61F 2002/465* (2013.01); *A61F 2002/4629* (2013.01); *A61F 2002/4681* (2013.01); *A61F 2002/4683* (2013.01); *A61F 2310/00023* (2013.01)

(58) Field of Classification Search
 CPC .......... A61F 2002/443; A61F 2002/448; A61F 2002/30487; A61F 2002/305; A61F 2002/3093; A61F 2/4455; A61F 2/447; A61F 2/4611
 See application file for complete search history.

(56) References Cited

U.S. PATENT DOCUMENTS

| | | | | |
|---|---|---|---|---|
| 5,370,697 | A * | 12/1994 | Baumgartner | A61F 2/442 623/17.15 |
| 5,571,191 | A | 11/1996 | Fitz | |
| 5,674,294 | A * | 10/1997 | Bainville | A61F 2/442 623/17.16 |
| 6,517,544 | B1 * | 2/2003 | Michelson | A61B 17/1659 606/80 |
| 7,008,226 | B2 | 3/2006 | Mayer et al. | |
| 7,335,205 | B2 | 2/2008 | Aeschlimann et al. | |
| 7,645,281 | B2 | 1/2010 | Marik | |
| 8,088,163 | B1 * | 1/2012 | Kleiner | A61F 2/4465 623/17.11 |
| 8,151,541 | B2 | 4/2012 | Aeschlimann et al. | |
| 8,357,201 | B2 | 1/2013 | Mayer et al. | |
| 8,403,938 | B2 * | 3/2013 | Aeschlimann | A61B 17/0401 606/93 |
| 8,663,297 | B2 | 3/2014 | Mayer et al. | |
| 8,685,100 | B2 | 4/2014 | Jodaitis et al. | |
| 8,814,920 | B2 | 8/2014 | Procter | |
| 8,951,254 | B2 | 2/2015 | Mayer et al. | |
| 9,398,927 | B2 | 7/2016 | Baehre et al. | |
| 9,402,725 | B2 | 8/2016 | Baumgartner et al. | |
| 9,901,459 | B2 * | 2/2018 | Faulhaber | A61F 2/4455 |
| 2003/0074063 | A1 * | 4/2003 | Gerbec | A61F 2/4455 623/16.11 |
| 2003/0195631 | A1 * | 10/2003 | Ferree | A61F 2/4425 623/17.16 |
| 2004/0030341 | A1 | 2/2004 | Aeschlimann et al. | |
| 2004/0034423 | A1 * | 2/2004 | Lyons | A61F 2/442 623/17.13 |
| 2004/0034430 | A1 * | 2/2004 | Falahee | A61F 2/4455 623/17.16 |
| 2004/0122424 | A1 * | 6/2004 | Ferree | A61B 17/1671 606/86 A |
| 2004/0193273 | A1 * | 9/2004 | Huang | A61F 2/442 623/17.12 |
| 2004/0210219 | A1 * | 10/2004 | Bray | A61B 17/7059 606/279 |
| 2004/0236342 | A1 * | 11/2004 | Ferree | A61B 17/025 606/102 |
| 2004/0243238 | A1 * | 12/2004 | Arnin | A61F 2/4425 623/17.12 |
| 2004/0249461 | A1 * | 12/2004 | Ferree | A61F 2/2846 623/17.11 |
| 2004/0267369 | A1 * | 12/2004 | Lyons | A61F 2/442 623/17.16 |
| 2005/0015150 | A1 * | 1/2005 | Lee | A61F 2/441 623/17.12 |
| 2005/0055098 | A1 * | 3/2005 | Zdeblick | A61B 17/1671 623/17.11 |
| 2005/0071008 | A1 * | 3/2005 | Kirschman | A61B 17/7059 623/17.11 |
| 2005/0131544 | A1 * | 6/2005 | Kuras | A61F 2/4425 623/17.13 |
| 2005/0159818 | A1 * | 7/2005 | Blain | A61F 2/4425 623/17.15 |
| 2005/0159819 | A1 * | 7/2005 | McCormack | A61B 17/1757 623/17.16 |
| 2005/0165485 | A1 * | 7/2005 | Trieu | A61F 2/442 623/17.13 |
| 2005/0165486 | A1 * | 7/2005 | Trieu | A61F 2/442 623/17.13 |
| 2005/0203626 | A1 * | 9/2005 | Sears | A61F 2/4425 623/17.11 |
| 2005/0277938 | A1 * | 12/2005 | Parsons | A61B 17/70 606/291 |
| 2006/0052870 | A1 * | 3/2006 | Ferree | A61B 17/025 623/17.11 |
| 2006/0206209 | A1 | 9/2006 | Cragg et al. | |
| 2007/0050030 | A1 * | 3/2007 | Kim | A61B 17/7059 623/17.11 |
| 2007/0198091 | A1 | 8/2007 | Boyer et al. | |
| 2007/0233135 | A1 | 10/2007 | Gil et al. | |
| 2007/0233262 | A1 * | 10/2007 | Arnin | A61F 2/4425 623/17.15 |
| 2007/0270968 | A1 * | 11/2007 | Baynham | A61F 2/447 623/17.11 |
| 2008/0077242 | A1 * | 3/2008 | Reo | A61F 2/441 623/17.15 |
| 2008/0077244 | A1 * | 3/2008 | Robinson | A61F 2/442 623/17.16 |
| 2008/0132949 | A1 * | 6/2008 | Aferzon | A61F 2/446 606/246 |
| 2008/0215156 | A1 * | 9/2008 | Duggal | A61B 17/1604 623/18.11 |
| 2009/0018560 | A1 | 1/2009 | Mayer et al. | |
| 2009/0131947 | A1 | 5/2009 | Aeschlimann et al. | |
| 2009/0138053 | A1 | 5/2009 | Assell et al. | |
| 2009/0171394 | A1 | 7/2009 | Abdou | |
| 2009/0192616 | A1 * | 7/2009 | Zielinski | A61F 2/4425 623/17.16 |
| 2009/0204152 | A1 | 8/2009 | Blain | |
| 2009/0222095 | A1 | 9/2009 | Johansonn et al. | |
| 2009/0234455 | A1 * | 9/2009 | Moskowitz | A61B 17/0642 623/17.11 |
| 2009/0240333 | A1 * | 9/2009 | Trudeau | A61F 2/44 623/17.13 |
| 2009/0264928 | A1 | 10/2009 | Blain | |
| 2010/0049179 | A1 | 2/2010 | Kanaoka et al. | |
| 2010/0094430 | A1 | 4/2010 | Krumdieck | |
| 2010/0215716 | A1 | 8/2010 | Troxel et al. | |
| 2011/0112650 | A1 | 5/2011 | Masini | |
| 2011/0208310 | A1 * | 8/2011 | Aschmann | A61B 17/7002 623/17.16 |

(56) References Cited

U.S. PATENT DOCUMENTS

| | | | |
|---|---|---|---|
| 2012/0109197 A1 | 5/2012 | Carl et al. | |
| 2012/0191189 A1* | 7/2012 | Huang | A61F 2/4425 623/17.11 |
| 2012/0323277 A1 | 12/2012 | Chervitz et al. | |
| 2012/0323326 A1 | 12/2012 | Boehm, Jr. | |
| 2013/0131821 A1 | 5/2013 | Cachia | |
| 2013/0190879 A1 | 7/2013 | Assell et al. | |
| 2014/0222147 A1 | 8/2014 | Muller et al. | |
| 2014/0277461 A1* | 9/2014 | Nebosky | A61F 2/44 623/17.11 |

FOREIGN PATENT DOCUMENTS

| | | |
|---|---|---|
| JP | 2010-528681 | 8/2010 |
| WO | 2008/034276 | 3/2008 |
| WO | 2008/095327 | 8/2008 |
| WO | 2009/109057 | 9/2009 |
| WO | 2010/045749 | 4/2010 |
| WO | 2010/096942 | 9/2010 |

\* cited by examiner

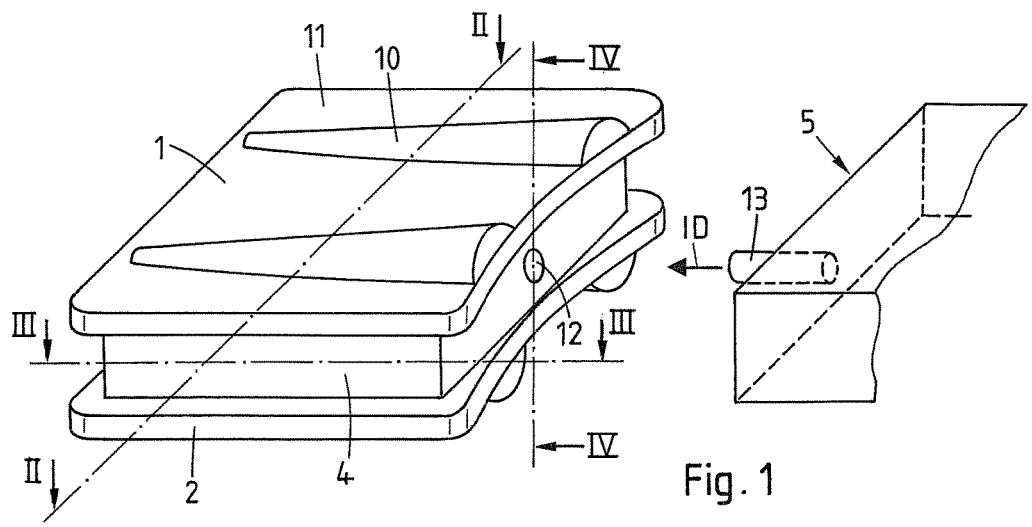
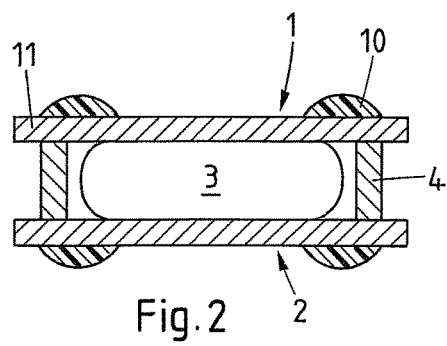 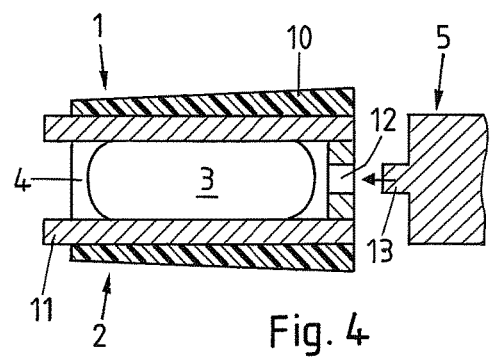
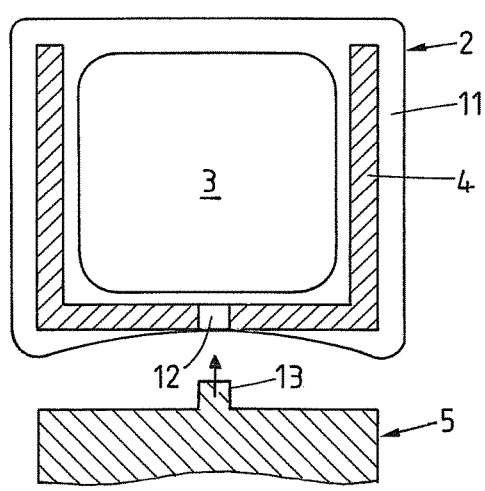 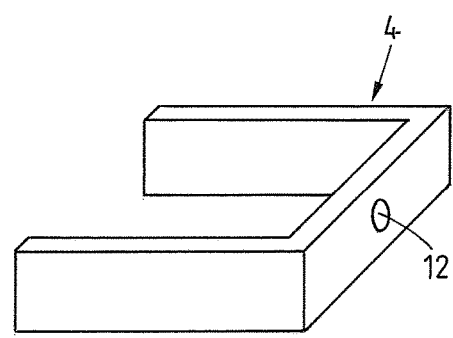

DEVICE FOR REPAIRING A HUMAN OR ANIMAL JOINT

BACKGROUND OF THE INVENTION

Field of the Invention

The invention is in the field of medical technology and is directed to a method and a device for repairing a human or animal joint, in particular a small synovial joint such as a human facet joint, a joint of the human hand or foot (including finger and toe joints), a sacroiliac joint, sternoclavicular joint, sternocostal articulation or a costovertebral joint, but also cartilaginous joints, in particular intervertebral joints. The expression "repairing a joint" is used herein in the sense of surgery concerning both articular surfaces of the joint by introducing a device in the joint and fastening it to both articular surfaces, wherein after the surgery, the joint will be capable of at least restricted articulation, i.e. the repair is not a so called joint fusion (no articulation capability after surgery) but it is e.g. a joint resurfacing (approximately full articulation capability maintained or restored).

Description of Related Art

The publication U.S. Pat. No. 5,571,191 (Fitz) discloses methods and devices for resurfacing human facet joints, wherein the device comprises two independent cap-like components to be fastened to the articular processes of the joint in two successive surgical steps, each one of the components constituting an artificial articular surface. WO 2008/034276 also discloses a method and a device for such resurfacing. For the surgery as proposed in both named cases, it is necessary to make the articular surfaces of the joint to be treated accessible either by dislocating or luxating the joint or by largely resecting the joint capsule and the related ligaments.

The publication US-2009/171394 (Abdou) discloses methods and devices for surgically treating human facet joints by providing in each one of the articular surfaces un undercut groove, the grooves being located opposite one another, and by introducing through a cannula a device into the grooves, wherein cannula and device have cross sections adapted to the pair of opposite undercut grooves. The device is initially retained in the grooves by a press fit, followed by osseointegration. The device comprises two device parts, of which one fits into each one of the pair of opposite undercut grooves. The device parts are separate from each other or they are connected to each other either rigidly or through an elastomeric portion. Depending on the choice of the type of device, after such surgery, the treated joint will allow full articulation (separate device parts), limited articulation (elastomeric connection between the device parts) or no articulation (rigidly connected device parts), i.e. joint fusion.

The publication WO2010/045749 (WW Technology), which is enclosed herein in its entirety by reference, describes devices and methods for fusing a small synovial joint in a human or animal patient, in particular a human facet joint, by introducing between the suitably prepared articular surfaces of the joint a fusion device and by anchoring the fusion device in both articular surfaces by in situ liquefaction of a material having thermoplastic properties and being suitably arranged on the fusion device, and by letting the liquefied material penetrate into bone tissue of the articular surfaces, where on re-solidification it constitutes a positive fit connection between the fusion device and the bone tissue. For the in situ liquefaction, application of vibrational energy (in particular ultrasonic vibration) to the fusion device is preferred and for restricting the liquefaction to desired locations and therewith preventing undue thermal load in tissue near the surgical site, thermoplastic materials (and preferably other materials comprised by the device) are chosen to be capable of vibration energy transmission with little loss (no inner liquefaction) such limiting liquefaction to interfaces between a vibrating element (device or device part) and a counter element (bone tissue or further device part), which interfaces are situated at locations where liquefaction and penetration is desired.

BRIEF SUMMARY OF THE INVENTION

It is the object of the invention to provide a method and a device for repairing a joint in human or animal patients, in particular a small synovial joint such as e.g. a human facet joint, or a cartilaginous joint such as e.g. a human intervertebral joint, wherein the repaired joint is to be capable of limited to full articulation after the repair operation, wherein both articular surfaces of the joint are to be treated simultaneously, and wherein the repair is to comprise introduction of a device between the suitably prepared articular surfaces and fixation of device portions in either one of these surfaces in one only surgical step, and with the aid of a material having thermoplastic properties and being liquefied in situ by application of vibratory energy.

These and other objects are achieved by the invention as defined in the claims.

As stated above in connection with the state of the art, targeted in situ liquefaction of a material having thermoplastic properties with the aid of vibratory energy for anchoring a device in hard tissue (in most cases bone tissue but also including suitable bone replacement material) can be achieved without undue thermal load on tissue of the surgical site, if the device is designed for being capable of transmitting vibratory energy with as little loss as possible from a proximal face contacted with a vibration tool to the site of desired liquefaction, i.e. to an interface between the vibrating device or a part thereof and a counter element (bone tissue or further device part). Such efficient energy transmission is achieved in the case of desired liquefaction at interfaces between device and hard tissue by designing the device to be a single rigid vibrator and by vibrating the whole device, and in the case of desired liquefaction between two device parts by designing the device to comprise two rigid parts, by vibrating one of the rigid parts and keeping the other part from being vibrated also. This requirement contrasts with the requirement of at least limited articulation of the joint after treatment, which necessitates two device parts to be able to articulate against each other, i.e. forbids a rigid connection therebetween.

The above named two contrasting requirements are reconciled according to the invention by designing the device for repairing the human or animal joint to comprise two articulating portions which are able to be articulated and possibly translated relative to each other and further equipping the device with a temporal connector portion which rigidly connects, at least for the time of the implantation, the two articulating portions.

In a first preferred group of embodiments, the device according to the invention comprises two articulating portions, a resilient interface portion arranged between the articulating portions and fixed to each one of the articulating portions, and, as temporal connector portion, a spreader being removably clamped between the articulating portions by the resilient force of the interface portion. The clamped spreader renders the device or part thereof rigid for the implantation procedure and is removed immediately after implantation of the device, or in a follow-up surgical procedure after an initial healing phase, in which the joint is immobilized by the spreader, or it is removed gradually by bio-resorption or bio-degradation. The interface portion remains in the joint for limiting articulation or is gradually removed by bio-resorption or bio-degradation after a first or second healing phase in which articulation of the joint is to be limited by the interface portion.

In a second group of exemplary embodiments, the device according to the invention comprises two articulating portions and, as temporal connector portion, a clamp which is capable to clamp the two articulating portions together such connecting them to form one rigid element. The device may further comprise an interface portion arranged between the articulating portions, wherein the interface portion is resilient and fixed or not fixed to the articulating portions, or is rigid and not fixed to the articulating portions, i.e. allowing articulation and/or translation of the articulating portions relative to each other. The clamp and possibly the interface portion is removed or bio-resorbed or bio-degraded as discussed for the first preferred group of embodiments.

In a third group of exemplary embodiments, the device according to the invention comprises two articulating portions and a rigid connector portion consisting of a bio-resorbable or bio-degradable material and being arranged between the two articulating portions and rigidly fixed to either one of the latter, the connector portion comprising a bio-resorbable or bio-degradable material. The connector portion is removed from between the articulating surfaces by bio-resorption or bio-degradation in a healing phase after the implantation, wherein during this healing phase initial immobilization of the joint by the connector portion gradually decreases to eventually leave the articulating portions independent of each other, i.e. with no limitation of the articulating capability of the joint or with such limitation as constituted by the form of the articulating surfaces of the articulating portions. Alternatively, the initially rigid connector portion may only partially be removed by bio-resorption or bio-degradation leaving a resilient or flexible interface portion between the articulating portions as discussed above for the first or second group of embodiments of the device according to the invention.

All embodiments of the device according to the invention constitute at least just before and in particular during the implantation procedure one piece which is pushed between the two articulating surfaces of the joint to be repaired. This means that for the implantation the named articulating surfaces need not to be made accessible by widely opening or dislocating the joint and are therefore particularly suitable for minimally invasive surgery. The fact that the device according to the invention is anchored in the articulating surfaces of the joint where cortical and cancellous bone are usually well developed and still does not need direct access to the articulating surfaces by opening the joint, makes lateral approach to hinge joints, in particular to small hinge joints such as e.g. interphalangeal and metacarpophalangeal joints in the human hand, not only possible but also advantageous.

As stated above, each one of the two articulating portions of the device according to the invention is anchored in bone tissue of one of the two suitably prepared articulating surfaces of the joint to be treated, with the aid of a material having thermoplastic properties and vibration energy or possibly in bone replacement material arranged at the articulating surfaces of the joint. Therein the vibration energy is transmitted to the device or to a part thereof from a proximal face and liquefaction is achieved at an interface between the device and bone tissue (or replacement material) of the two articulating surfaces of the joint or at interfaces between device parts, the latter interfaces being located near bone tissue (or replacement material) of the two articulating surfaces of the joint.

The basis of the named anchoring technique is the in situ liquefaction of a thermoplastic material having mechanical properties suitable for a mechanically satisfactory anchorage of an implant in hard tissue (e.g. bone tissue or corresponding replacement material), wherein the material in its liquefied state has a viscosity which enables it to penetrate into natural or beforehand provided pores, cavities or other structures of the hard tissue, and wherein an only relatively small amount of the material is liquefied such that a non-acceptable thermal load on the tissue is prevented. When re-solidified, the thermoplastic material which has penetrated into the pores, cavities or other structures constitutes a positive fit connection with the hard tissue.

Suitable liquefaction combined with an acceptable thermal loading of the tissue and suitable mechanical properties of the positive fit connection is achievable by using materials with thermoplastic properties having initially a modulus of elasticity of at least 0.5 GPa and a melting temperature of up to about 350° C. and by providing such material e.g. on an implant surface, which on implantation is pressed against the hard tissue, preferably by introducing the implant into an opening (e.g. bore) which is slightly smaller than the implant or by expanding the implant in an opening which originally is slightly larger than the implant (expansion e.g. by mechanically compressing or buckling of the implant). For anchoring the implant in the hard tissue, the implant is subjected to vibration of a frequency preferably in the range of between 2 and 200 kHz (preferably ultrasonic vibration) by applying e.g. the sonotrode of an ultrasonic device to the implant. Due to the relatively high modulus of elasticity the thermoplastic material is able to transmit the ultrasonic vibration with such little damping that inner liquefaction and thus destabilization of the implant does not occur, i.e. liquefaction occurs only where the thermoplastic material is in contact with the bone tissue and is therewith easily controllable and can be kept to a minimum.

Instead of providing the material having thermoplastic properties on the surface of the implant (disclosed e.g. in U.S. Pat. No. 7,335,205 or 7,008,226), it is possible also to provide the material having thermoplastic properties in a perforated sheath and to liquefy it within the sheath and press it through sheath perforations to the surface of the implant and into the pores or cavities of the hard tissue (disclosed e.g. in U.S. Pat. Nos. 7,335,205 and 7,008,226) and/or it is possible to liquefy the material having thermoplastic properties between two implant parts of which one is vibrated and the other one serves as counter element, the interface between the two implant parts being positioned as near as possible to the hard tissue (as disclosed in the publications US 2009/131947 and WO2009/109057).

Materials having thermoplastic properties suitable for the device and the method according to the invention are thermoplastic polymers, e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyam ides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of BOhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate by DSM, in particular type 65D and 75D). An overview table of polymers and applications is listed in Wintermantel, page 150; specific examples can be found in Wintermantel page 161 ff. (PE, Hostalen Gur 812, HOchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the immplant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), JA Juhasz et al. Biomaterials, 2004 March; 25(6):949-55. Particulate filler types include: coarse type: 5-20 μm (contents, preferentially 10-25% by volume), sub-micron (nanofillers as from precipitation, preferentially plate like aspect ratio >10, 10-50 nm, contents 0.5 to 5% by volume).

Specific examples of bio-degradable filled polymer material are PLLA filled with tricalciumphosphate or PDLLA 70%/30% (70% L and 30% D/L, LR706 by BOhringer) filled with up to 30% biphasic calciumphosphate.

Portions of the implantable device or device part which do not serve the anchoring function may consist of any suitable material (e.g. polymer, metal, ceramic, glass) which material may be bio-resorbable, bio-degradable or not and may have thermoplastic properties or not. Where such materials are to be in contact with bone tissue they preferably have surfaces equipped for furthering osseointegration, i.e. with per se known surface structures and/or coatings.

The devices and methods according to the invention are in particular suitable for minimally invasive surgery but are also applicable in open surgery.

BRIEF DESCRIPTION OF THE DRAWINGS

The invention is described in further detail in connection with the appended Figs., wherein:

FIGS. 1 to 5 show an example of the first preferred group of embodiments of the device according to the invention, the device comprising two articulating portions, a resilient interface portion and a temporal connector portion in the form of a spreader;

FIG. 1 is a partially exploded perspective view of the complete device;

FIG. 2 is a sectional elevation view taken along section II-II of FIG. 1 perpendicular to implantation direction;

FIG. 3 is a sectional plan view taken along section III-Ill of FIG. 1;

FIG. 4 is a sectional elevation view taken along section IV-IV of FIG. 1 parallel to implantation direction;

FIG. 5 is a perspective view of the spreader;

DETAILED DESCRIPTION OF THE INVENTION

Figure 6:
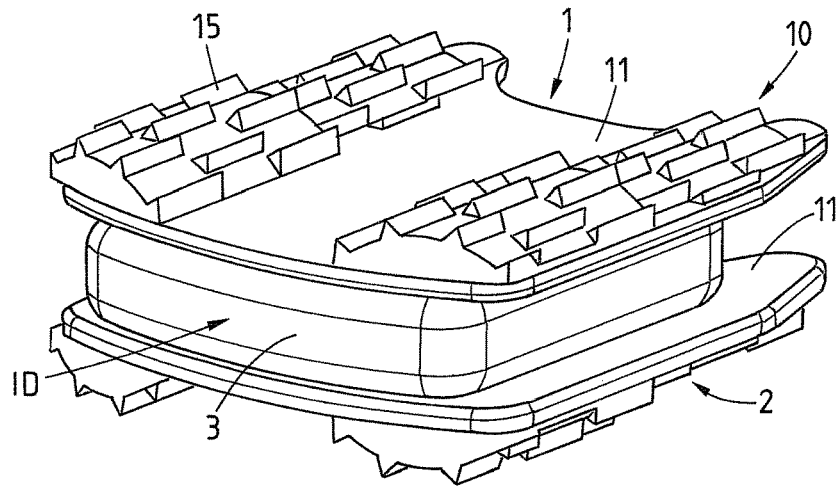
FIG. 6 is a perspective view of a further exemplary embodiment of the first preferred group, illustrated without showing the connector portion.

FIGS. 1 to 5 show an example of the first, preferred group of embodiments of the device according to the invention. The device comprises two articulating portions 1 and 2, a resilient interface portion 3 and a connector portion 4 in the form of a spreader. FIG. 1 is a three dimensional representation of the complete device and further shows a distal end of a vibration tool 5 used for implanting the device. FIGS. 2, 3 and 4 are sections through the complete device (FIG. 2: section line II-II perpendicular to the implantation direction ID, FIGS. 2 and 3: section lines III-III and IV-IV parallel to the implantation direction ID, the section lines being indicated in FIG. 1). FIG. 5 is a three dimensional representation of the connector portion only.

The articulating portions 1 and 2 face against each other with their inner sides (articulating surfaces of the articulating portions) and comprise on their outer sides the material having thermoplastic properties, e.g. in the form of protruding ridges 10 extending parallel to the implantation direction ID, wherein the protruding ridges 10 of the material having thermoplastic properties may be fixed in an undercut groove (not shown) or on a rough or porous surface portion of a carrier plate 11 being made of a different material (e.g. metal or ceramic material) and, on their surfaces facing the bone tissue, may carry energy directors in the form of edges or small peaks protruding from a main surface. It is possible also to manufacture the whole articulating portions 1 and 2 of the material having thermoplastic properties.

The resilient interface portion 3 is arranged between the two articulating portions 1 and 2 and is fixed to the inner sides thereof, i.e. to the surface of the carrier plate 11 opposite to its surface carrying the ridges 10. The interface portion 3 is capable of being compressed and stretched in particular in a direction perpendicular to the inner sides of the articulating portions 1 and 2 or between the carrier plates 11 respectively, thereby not only changing the distance between these carrier plates but possibly also an angle therebetween. The interface portion 3 may also be deformable such that it allows limited translation between the two articulation portions 1 and 2 or the two carrier plates 11 respectively. The interface portion 3 is e.g. an elastomeric construct (e.g. made of an elastomer or liquid or gas filled container having resilient walls).

The connector portion 4 is designed for being positioned between the articulating portions 1 and 2 or the carrier plates 11 respectively and has a height between the carrier plates 11 which is large enough for stretching the interface portion 3 such that forces normally occurring during handling and implantation of the device are not able to spread the articulating portions further, i.e. to release the connector element 4 from being clamped between the carrier plates 11 by the resilient force of the interface portion 3. The connector portion 4 has preferably the form of a U surrounding the interface portion 3 on a proximal side and both lateral sides. The central member of the U-shaped connector portion preferably comprises means for attaching the distal end or a vibration tool 5 to it, e.g. a bore 12 into which a protrusion 13 arranged on this distal tool end (e.g. thread or press fit connection). Alternatively, the named attachment means are e.g. a protrusion on the connector portion 4 and a corresponding bore on the tool 5, or a corresponding pair of cone and tapering bore. The attachment means are designed to be capable of transmitting the vibrations of the tool 5 into the connector portion 4 and to stand not only the compressive force during implantation but also the tensile load on pulling the connector portion 4 away from the implanted rest of the device (articulating portions 1 and 2 and interface portion 3) after the anchoring step.

For facilitating the removal of the connector portion 4 on completion of the anchoring step, it is advised to provide surfaces of the connector portion 4, at least where in contact with the articulating portions 1 and 2, of materials which are not prone to fretting or ceasing on removal of the connector portion (relative movement with high friction due to pressure). For carrier plates 11 of titanium it is therefore proposed to use for the connector portion 4 or the corresponding surface thereof a different metal, e.g. stainless steel or aluminum, or to coat with e.g. PEEK such surfaces of a less suitable material (e.g. same metal as articulating portions, e.g. titanium).

The vibration tool 5 has a distal face, which is preferably adapted in form and size to the proximal face of the connector portion 4, and a proximal end which is connected or connectable to a vibration source (e.g. ultrasonic device, possibly with booster).

Implantation of the device according to FIGS. 1 to 5 in a joint, e.g. a human facet joint) comprises the following steps:

The articular surfaces of the joint are prepared by exposing the subchondral bone of the articular surfaces at least where the material having thermoplastic properties is to be liquefied and to penetrate the bone tissue. The joint is e.g. fixed in a distracted or non-distracted configuration and two bores (two pairs of opposite grooves one in each articular surface of the joint) are drilled in a direction about parallel to the articular surfaces, the bores being dimensioned to be slightly smaller than the ridges 10 of the device. Further areas of the articular surfaces, e.g. to be in contact with the carrier plates 11 may be decorticated to enhance osseointegration with the preferably correspondingly equipped outer surfaces of the carrier plates 11.

The device comprising the two articulating portions 1 and 2, the interface portion 3 and the connector portion 4 clamped between the articulating portions is mounted to the distal end of the vibration tool 5 and the proximal end of the vibration tool is connected with the vibration source.

The device is positioned with its distal end in or at the entrance to the gap between the prepared articulating surfaces of the still fixed joint, the ridges of the material having thermoplastic properties being aligned with the bores or grooves in the articulating surfaces respectively.

The device is pushed into the gap between the two articular surfaces and simultaneously the vibration tool is vibrated, such advancing the device into the gap, liquefying the material having thermoplastic properties at least where it is in pressing contact with the bone tissue and letting the liquefied material penetrate the bone tissue.

The vibration source is switched off and the liquefied material is allowed to re-solidify, while the pressing force is preferably maintained.

The vibration tool 5 together with the connector portion 4 is pulled away from the joint wherein it may be advantageous to release fixation of the joint and to lightly distract the implanted articular portions using a suitable distraction tool and/or to counteract the pulling force with a suitable tool acting on the proximal faces of the articulating portions 1 and 2.

Fixation of the joint during at least the step of implanting and anchoring the device in the joint is preferred, such that neither the forcing of the device into the joint nor the liquefied material being pressed into the bone tissue of the articular surfaces can change the relative position of the articulating surfaces of the joint during the implantation. Such fixation of the joint is e.g. achieved by positioning a distal face of a cannulated guide tool against the bone surface of the implantation site, wherein sharp protrusions provided on this distal face are forced into the bone surface on either side of the pair of articular surfaces. Therein the axial channel of the guide tool is preferably not only adapted for guiding the device to the joint and into the joint but also to instruments used for locating and preparing the joint for the implantation, i.e. to instruments such as e.g. a joint finder whose distal end, for locating the joint, is forced between the articular surfaces of the joint to be repaired, a drill and/or a cutting tool (or possibly a drill guide or cutting tool guide) for preparing the articular surfaces. This means that the guide tool is fixed on the bone surface in one of the first steps of the implantation procedure and is removed in one of the last steps, therebetween serving for fixing the joint and for guiding the tools necessary for the surgery.

The whole implantation method is preferably carried out in a minimally invasive manner, i.e. with the aid of a cannula or with the aid of the above mentioned guide tool through which the device and all necessary tools are guided to the implantation site. A set of tools which is suitable for the method is disclosed in the publication WO-2010/045749 (WW Technology). However, use of the device and the method according to the invention is possible also in open surgery.

The device and the implantation method described above in connection with FIGS. 1 to 5 can be varied without departing from the basic idea of the invention e.g. in the following manner, wherein the listed variations may be combined with each other in various ways:

- The interface portion 3 has the shape of a round disk and the connector portion 4 the shape of a half circle.
- The interface portion 3 has a different thickness on either side of a middle line extending parallel to the implantation direction, i.e. the two articulating portions 1 and 2 are angled relative to each other.
- The interface portion has anisotropic deformation qualities by being made of an anisotropic material, e.g. by comprising a matrix material which is filled in an anisotropic manner, by comprising a matrix material in which an anisotropic structure of a stiffer material in integrated, or by comprising an anisotropic pattern of pores or cavities (see also FIG. 8).
- The interface portion 3 comprises two or more than two sections and the connector portion 4 extends between the these sections instead of around one only interface portion 3.
- The articulating surfaces of the articulating portions 1 and 2 are not even but e.g. curved, wherein the curvature of one articulating surface may be different from the curvature of the other articulating surface.
- The articulating surface of one articulating portion is larger than the articulating surface of the other articulating portion.
- Instead of comprising two or more than two ridges 10 of the material having thermoplastic properties, each articulating portion 1 or 2 comprises a complete or partial coating of the material having thermoplastic properties and no grooves are provided in the articulating surfaces of the joint.
- Depending on the character of the bone tissue in which the device is to be anchored it may not be necessary to remove bone tissue for providing the grooves for accommodation of the ridges 10, wherein in such a case the ridges may be equipped e.g. with sharp edges oriented parallel to the implantation direction for grooving the bone tissue by compressing or displacing it.
- The distal face of the vibration tool 5 is adapted for transmission of the vibration not only to the connector portion 4 but in addition or alternatively to the proximal faces of the articulating portions 1 and 2.
- The connector portion 4 is made of a bio-resorbable or bio-degradable material and is not removed after implantation but gradually resorbed or degraded. In such a case it is not necessary that the connector portion 4 extends to the proximal face of the device and the vibration may be coupled into the device through the proximal faces of the articulating portions 1 and 2, which are preferably mounted on the vibration tool 5 in a similar manner as described for the connector portion 4.
- The connector portion 4 is not connected to the vibration tool and comprises means for being gripped with a corresponding removal tool.
- The connector portion 4 is not removed immediately after implantation of the device but in a second surgical operation, wherein a removal tool may be connected to the connector portion 4 in the same way as the vibration tool 5 is connected to it for implantation.
- Instead of the ridges 10 consisting of the material having thermoplastic properties and being integral parts of the articulating portions 1 and 2, the articulating portions 1 and 2 comprise perforated sheaths or tunnels into which pins of the material having thermoplastic properties are pushed while being vibrated (see FIG. 13). In such a case, it is not the whole device which as vibrated but only part thereof, namely the pins, and liquefaction of the material having thermoplastic properties is achieved between the vibrating pins and the rigid rest of the device at interfaces inside the perforated sheaths or tunnels to flow through the perforation into the neighboring bone tissue, wherein the rest of the device made rigid by the connector portion and positioned between the articulating surfaces of the joint is prevented from vibrating together with the pins. There need to be at least two pins of the thermoplastic material, one for each articulating portion, preferably four, wherein all these pins may be vibrated in succession or simultaneously using a corresponding forked vibration tool.
- Instead of the ridges 10 consisting of the material having thermoplastic properties and being attached to the carrier plates 11, the device comprises separate pins of the material having thermoplastic properties and the carrier plates comprise corresponding grooves to be placed opposite the grooves provided in the articular surfaces of the joint (see e.g. FIG. 7). For anchoring the pins simultaneously in the bone tissue and in the carrier plate, the pins are pushed while being vibrated between articular surface and carrier plate of the device positioned between the articular surfaces of the joint. Also in this case, the rigidity of the device caused by the connector portion 4 keeps the device firmly in the joint while the pins are positioned and anchored and prevents loss of energy through vibration of device portions other than the pins.

One skilled in the art will easily adapt suitable ones of the above listed variations of the exemplary embodiment of the device according to FIGS. 1 to 5 for further embodiments of the device according to the invention as illustrated in the further Figs. and as described below in connection with these further Figs.

Figure 7:
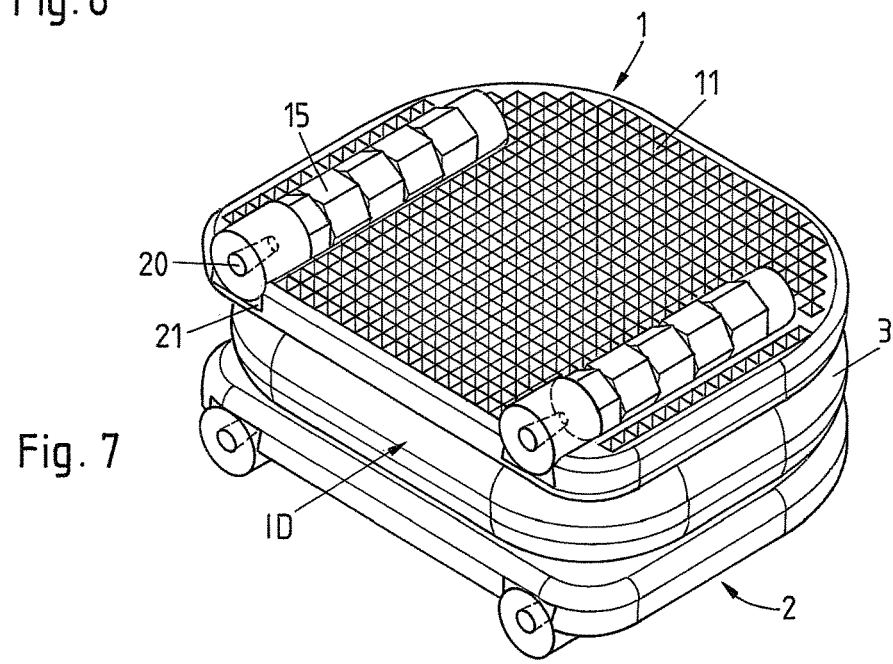
FIG. 7 is a perspective view of a further exemplary embodiment of the first preferred group, illustrated without showing the connector portion.

FIGS. 6 and 7 show in more detail two further examples of the first, preferred group of embodiments of the device according to the invention. Each one of the two illustrated devices comprise two articulating portions 1 and 2 and a resilient interface portion 3 positioned between the two articulating portions and attached thereto. The connector portion is not shown in FIGS. 6 and 7 but is supposed to be of a similar shape as shown in FIGS. 1 to 5.

The device according to FIG. 6 is very similar to the one according to FIGS. 1 to 5, wherein the ridges 10 of the material having thermoplastic properties are illustrated with energy directors in the form of longitudinally protruding small ridges or edges 15 extending along part of the ridge length and being offset relative to each other in the direction of this length.

The device according to FIG. 7 comprises instead of ridges 10, pins 20 of the material having thermoplastic properties which are accommodated in grooves 21 on the outer surface of the carrier plates 11 and protruding from these grooves. The same as the ridges 10 shown in FIG. 6, the pins 20 are equipped with edges 15 running along part of the pin length and being arranged offset to each other along the pin length. The pins 20 are either fixed in the grooves 21 as stated above and implantation of the device is carried out as described above for the device according to FIGS. 1 to 5. Alternatively, the pins 20 are separate device parts and for implantation, the device without the pins is first positioned between the articular surfaces of the joint to be treated, wherein each groove 21 on the outer side of a carrier plate 11 is facing a groove in the prepared articulating surface of the joint. Then a pin is pushed into every opening formed by one of the grooves in the articular surface of the joint and an opposite groove 21 in the carrier plate 11, while being vibrated for liquefaction of the material having thermoplastic properties to be liquefied where in contact with the bone tissue on the one side and with the material of the carrier plate 11 on the other side and to thereby be anchored on both sides.

The carrier plates 11 shown in FIG. 7 consist e.g. of titanium and have a structured or rough outer surface suitable for furthering osseointegration. Such osseointegration may replace the anchorage of the device in the bone tissue of the joint via the material having thermoplastic properties such that the pins 20 may consist of a bio-resorbable or bio-degradable material.

Figure 8:
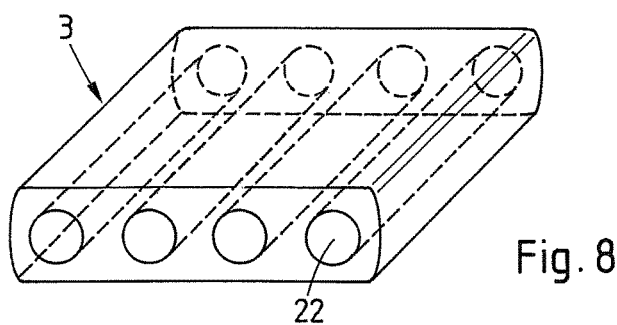
FIG. 8 is a perspective view that shows a further embodiment of a resilient interface portion applicable e.g. in the devices as illustrated in FIGS. 1 to 7.

FIG. 8 shows an example of a resilient interface portion 3 which is e.g. suitable for the devices as illustrated in FIGS. 1 to 7. The interface portion 3 comprises bores 22 with substantially parallel axes (or other cavities or pores arranged in parallel rows or other arrangements with one principal direction). This interface portion 3 has anisotropic characteristics, as mentioned further above, in that it offers less resistance to shear and bending forces acting in planes oriented perpendicular to the bore axes than to shear and bending forces acting in planes oriented parallel to the bore axes. With such equipped interface portions it becomes possible to mimic physiologically the range of motion and motion restraints towards the extremata of joint movement.

Figure 9:
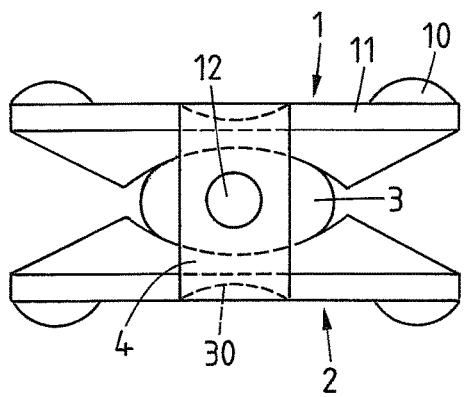
FIG. 9 is an elevation view that shows an example of the second group of embodiments of the device according to the invention, the device comprising two articulating portions, an interface portion and a connector portion in form of a clamp (viewed parallel to the implantation direction)
Figure 10:
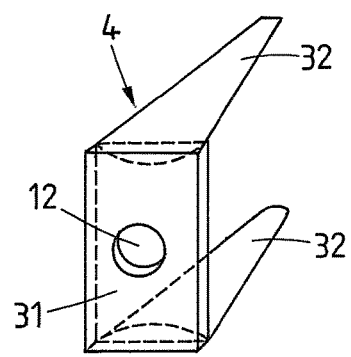
FIG. 10 is a perspective view that shows the connector portion or clamp of the device according to FIG. 9.

FIGS. 9 and 10 illustrate an example of a second group of embodiments of the device according to the invention. The device comprises two articulating portions 1 and 2 with e.g. ridges 10 of the material having thermoplastic properties and with a carrier plate 11, and it further comprises an interface portion 3 arranged between the articulating surfaces of the articulating portions 1 and 2, and a connector portion 4 in the form of a clamp. FIG. 9 shows the complete device viewed parallel to the implantation direction, FIG. 10 shows the connector portion 4 only. In contrast to the first group of embodiments of the device according to the invention, in the devices of the second group the articulating portions 1 and 2 are clamped together by the connector portion 4 instead of being spread apart. This means that the interface portion 3 may be rigid and not attached to either one of the articulating portions or it may be resilient and attached to both articulating portions or not.

The articulating portions 1 and 2 of the device according to FIG. 9 have concave inner sides and the interface portion 3 constitutes a separate item in the form of a free flattened sphere of a resilient or non-resilient material accommodated between these concave inner sides. This specific form of the articulating surfaces of the articulating portions 1 and 2 and of the interface portion 3 are not a condition for the second group of embodiments of the device according to the invention. These forms may also correspond to any form illustrated in the previous figures or described in the exemplary variations listed above for the device according to FIGS. 1 to 5.

The temporal connector portion 4 of the device according to FIGS. 9 and 10 is U-shaped with a central member 31 and two leg members 32 attached to the central member, the members of the connector portion 4 being dimensioned for the leg members 32 to fit in grooves 30 running parallel to the ridges 10 on the outer side of the carrier plates 11 and they are further dimensioned to exert a pressing force on the pair of the articulating portions 1 and 2. As discussed further above, the central member 31 of the connector portion 4 is preferably equipped for being connected to a distal end of a vibration tool, e.g. with a bore 12. As discussed further above, the temporal connector portion 4 is removed after the step of anchoring the articulating portions 1 and 2 in the bone tissue of the articulating surfaces of the joint by pulling the connector portion away from the joint, wherein it may be advantageous to press the articulating portions 1 and 2 against each other and/or to counteract the pulling by pressing the articulating portions 1 and 2 into the joint.

Figure 11:
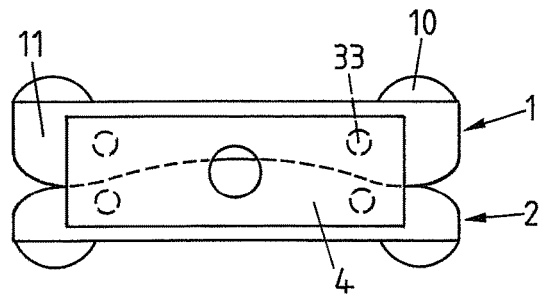
FIG. 11 is an elevation view that shows a further example of the second group of embodiments of the device according to the invention, the device comprising two articulating portions and a connector portion in form of a clamp (viewed parallel to the implantation direction)
Figure 12:
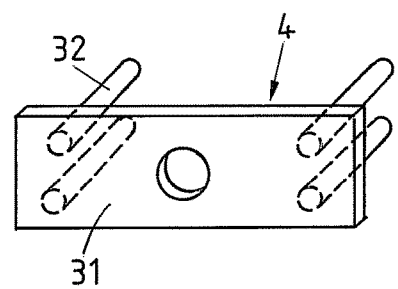
FIG. 12 is a perspective view that shows the connector portion or clamp of the device according to FIG. 11.

FIGS. 11 and 12 illustrate a further example of the second group of embodiments of the device according to the invention. FIG. 11 shows the complete device comprising two articulating portions 1 and 2, no interface portion and a temporal connector portion 4 clamping the two articulating portions against each other; FIG. 12 shows the connector portion 4 only. This connector portion 4 of the present embodiment comprises a central member 31 and in this case four leg members 32, which fit into bores 33 extending parallel to the implantation direction, two in each one of the articulating portions 1 and 2 and which are dimensioned and equipped for exerting a pressing force biasing the two articulating portions 1 and 2 against each other. Implantation and removal of the connector portion 4 are carried out as discussed for the previously described devices.

Figure 13:
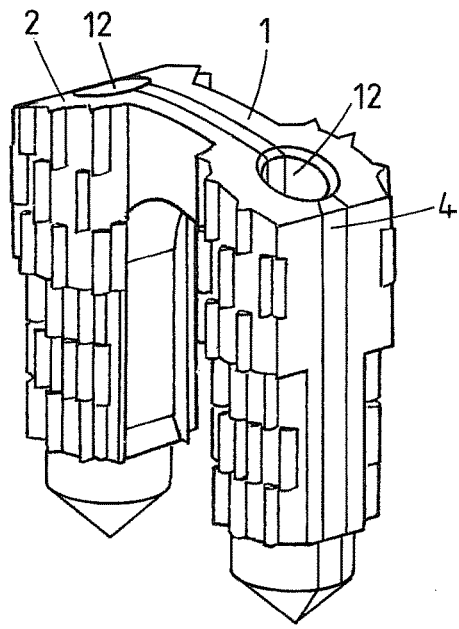
FIG. 13 is a perspective view that shows an example of the third group of embodiments of the device according to the invention, the device comprising two articulating portions being rigidly connected by a rigid and bio-degradable connector portion.

FIG. 13 shows an example of the third group of embodiments of the device according to the invention. This device comprises again two articulating portions 1 and 2 and a temporal connector portion 4 which connects the two articulating portions 1 and 2 rigidly by being rigid itself and by being rigidly connected to either one of the articulating portions 1 and 2. The connector portion 4 is arranged between the articulating surfaces of the articulation portions 1 and 2 and is made of a quickly bio-resorbable or bio-degradable or water-soluble material and therefore does not need to be removed by the surgeon. The device according to FIG. 13 comprises two bores 12 for being releasably connected with a vibration tool.

For initial blocking of joint movement e.g. for healing associated soft tissue damage and/or hard tissue fractures (possible additional damages which may be caused by the same trauma as the joint damages to be repaired in the manner presently discussed) it may be advantageous to use for the connector portion 4 a material capable of maintaining its rigidity for a longer time (preferably for 2 to 8 weeks). Polymers suitable for such prolonged but still temporal joint blocking or such longer term connector portion respectively are e.g. copolymers of lactic and glycolic acid or collagen based polymers, which are water soluble or bio-degradeable depending on their degree of cross-linking.

Apart from the bio-resorbable or bio-degradable material the connector portion 4 may further comprise non-resobable or non-degradable regions (not shown) which constitute a potential interface portion in the form of a resilient or flexible connection between the articulating portion 1 and 2 which limits articulation and possibly translation between the articulating portions once the resorbable or degradable part of the connector portion 4 is resorbed or degraded.

Figure 14:
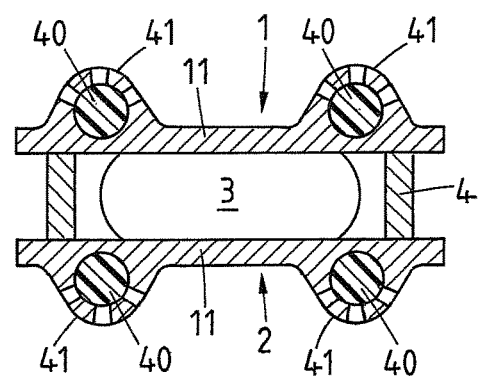
FIG. 14 is a sectional elevation view that illustrates a further example of the first group of embodiments of the device according to the invention.

FIG. 14 shows a section (similar to FIG. 3) through a further example of the first group of embodiments of the device according to the invention. As already mentioned further above, in this embodiment the material having thermoplastic properties is present in the form of a plurality of thermoplastic pins 40 which fit into perforated (or fenestrated) sheaths 41 or tunnels, which are arranged parallel to the implantation direction on the outer surface of the carrier plates 11 and protruding from the latter, or which are arranged in the carrier plates and not protruding from them. In FIG. 14 the thermoplastic pins are illustrated positioned inside the perforated sheaths 41. The perforations of the sheaths or tunnels are located on the outer side of the articulating portions 1 and 2 and are dimensioned such that the liquefied material of the thermoplastic pins 40 is capable of flowing unhindered to the outside of the sheathes 41 or tunnels for being capable of penetrating into the bone tissue of the articulating surfaces of the joint to be treated.

On implantation, the device according to FIG. 14 is positioned, with or without the pins 40 inside the sheaths 41, between the articulating surfaces of the joint to be treated. Then the pins 40 are pushed into the sheaths or tunnels while being vibrated. The pin material is liquefied on the interface between the pin and the inside surface of the sheath 41 or tunnel, in particular in locations where either one of the named inside wall or the pin comprises energy directors, and flows through the perforations to penetrate adjacent bone tissue. For targeted liquefaction, the named energy directors are preferably arranged on the inside surface of the sheath or tunnel in the region of the perforations.

The implantation of the device as shown in FIG. 14 is carried out much the same as described above for the device as shown in FIG. 6 and comprising separate pins 20.

Of course it is possible also to equip embodiments of the second and third group of embodiments of the device according to the invention with sheaths or tunnels as shown in FIG. 14 and implanting them with the method as described above for the device according to FIG. 14.

What is claimed is:

1. A device for treating a human or animal joint, the joint comprising two articulating surfaces and the device comprising:
    two articulating portions capable of at least limited articulation relative to each other and being equipped for being fixed one in each one of the articulating surfaces with the aid of a material having thermoplastic properties and vibration energy, wherein the material having thermoplastic properties is arranged on outer sides of each articulating portion,
    a temporal connector portion being removably arranged between the two articulating portions, wherein the temporal connector portion, when arranged between the two articulating portions, connects the two articulating portions to form a rigid, non-articulating entity constituting one piece at least during an implantation procedure, said temporal connector portion being configured to be removed separately from said two articulating portions after having connected the two articulating portions at least for the time of the implantation procedure,
    and an interface portion that is arranged between inner sides of the articulating portions, wherein the interface portion is elastic and fixed to each one of the inner sides of the two articulating portions and wherein the temporal connector portion is a spreader that is clamped between the inner sides of the articulating portions and retained in a clamped position by elasticity of the interface portion.

2. The device according to claim 1, wherein the device comprises carrier plates and wherein articulating portions comprise the material having thermoplastic properties in at least one of: ridges protruding from outer surfaces of the carrier plates, a coating of said outer surface of the carrier plates, in pins arranged in grooves on outer sides of the carrier plates, and in perforated sheaths or tunnels on or in the carrier plates.

3. The device according to claim 1, wherein the whole articulating portions are made of the material having thermoplastic properties.

4. The device according to claim 1, wherein the material having thermoplastic properties is arranged on outer sides of each articulating portion such that the material having thermoplastic properties is pressed against exposed subchondral bone tissue during the implantation procedure.

5. The device according to claim 1, wherein the two articulating portions are capable of at least limited translation relative to each other.

6. The device according to claim 1, wherein the interface portion is elastic or rigid, and wherein the temporal connector portion is a clamp capable of clamping together the two articulating portions.

7. The device according to claim 1, wherein the temporal connector portion is rigid and is arranged between the two articulating portions and rigidly attached to each one of the articulating portions and wherein the temporal connector portion is at least partly made of a bio-resorbable or bio-degradable material.

8. The device according to claim 6, wherein the interface portion is made of a bio-resorbable or bio-degradable material.

* * * * *